United States Patent [19]

Kitko

[11] 4,248,827

[45] Feb. 3, 1981

[54] METHOD FOR SANITIZING TOILETS

[75] Inventor: David J. Kitko, West Chester, Ohio

[73] Assignee: The Procter & Gamble Company, Cincinnati, Ohio

[21] Appl. No.: 915,027

[22] Filed: Jun. 12, 1978

[51] Int. Cl.³ .......................... E03D 9/02; A61L 2/16
[52] U.S. Cl. ........................................ 422/37; 4/227; 4/228; 4/DIG. 9
[58] Field of Search ...................... 422/37; 4/227, 228, 4/DIG. 9

[56] References Cited

U.S. PATENT DOCUMENTS

| 1,798,090 | 3/1931 | Lebegue | 4/220 UX |
|---|---|---|---|
| 3,121,236 | 2/1964 | Yadro et al. | 4/228 |
| 3,243,377 | 3/1966 | Stolar | 252/100 |
| 3,318,815 | 5/1967 | Remler et al. | 252/106 |
| 3,339,801 | 9/1967 | Hronas | 4/228 X |
| 3,341,074 | 9/1967 | Pannutti | 4/227 X |
| 3,355,392 | 11/1967 | Cantor et al. | 252/99 |
| 3,378,495 | 4/1968 | Buck | 422/37 X |
| 3,444,566 | 5/1969 | Spear | 4/228 |
| 3,503,884 | 3/1970 | Chirash et al. | 252/95 |
| 3,504,384 | 4/1970 | Radley et al. | 4/228 |
| 3,741,805 | 6/1973 | Crotty et al. | 422/37 X |
| 3,793,211 | 2/1974 | Kohlepp | 252/99 |
| 3,831,205 | 8/1974 | Foley | 4/228 |
| 3,936,385 | 2/1976 | Cheng | 252/99 |
| 4,036,407 | 7/1977 | Slone | 4/228 X |
| 4,216,027 | 8/1980 | Wages | 4/228 X |

FOREIGN PATENT DOCUMENTS 2133710  1/1973  Fed. Rep. of Germany .

OTHER PUBLICATIONS

Herring; Soap Perf. & Cos. #10; 10/77; pp. 426–428.

Primary Examiner—Barry S. Richman
Attorney, Agent, or Firm—Ronald L. Hemingway; Richard C. Witte

[57] ABSTRACT

A method for sanitizing toilets wherein a hypochlorite sanitizing agent and an oxidizable dye are dispensed from separate dispensing means into the toilet flush water to provide a color to the bowl water. The color disappears within a short time after the flush, thereby providing a visual indicator of the activity of the sanitizing agent.

13 Claims, No Drawings

METHOD FOR SANITIZING TOILETS

TECHNICAL FIELD

The present invention relates to the automatic sanitizing of flush toilets by the dispensing of a bleachable dye and a hypochlorite sanitizing agent to the toilet bowl with each flush. The dye is bleached by the hypochlorite to a colorless state within a short time after flushing, thereby providing a visual signal of the activity of the hypochlorite.

BACKGROUND ART

This invention relates to a method of sanitizing a toilet bowl. More particularly, it relates to a method wherein a hypochlorite sanitizing agent and a water-soluble dye, which is oxidizable by the hypochlorite from a colored to a colorless state, are automatically dispensed from separate dispensing means to the toilet bowl during flushing. The water in the bowl at the end of the flush is colored by the dye. However, the dye is oxidized to a colorless state within a short time thereby providing a visual signal that the hypochlorite sanitizing agent is present and "acting" in the bowl.

Automatically dispensed toilet bowl cleaning and/or sanitizing products, which contain dyes to provide a visual signal to the user that product is being dispensed, are well known. Such products are sold in the United States under the brand names VANISH AUTOMATIC (Drackett Products), TY-D-BOL AUTOMATIC (Knomark, Inc.) and SANIFLUSH AUTOMATIC (Boyle-Midway). None of these products contains a hypochlorite sanitizing agent and all of them provide a color to the bowl water which persists between flushings. U.S. Pat. No. 3,504,384, Radley et al., issued Apr. 7, 1970, discloses a dual compartment dispenser for automatically dispensing a hypochlorite solution and a surfactant/dye solution to the toilet bowl during flushing. The dye which is taught in the patent is Disulfide Blue VN150. It is believed that the dye referred to in Radley et al. is actually Disulphine Blue VN150 (Color Index No. 42045). This dye has been found by the present applicant to be quite resistant to oxidation to a colorless state by hypochlorite; thus, it too provides a persistent color to the toilet bowl water, even in the presence of the hypochlorite.

A persistent color in the toilet bowl water has certain attendant negatives. The dye can cause staining of the toilet bowl itself or of deposits (such as water hardness deposits) which accumulate on the surfaces of the bowl between manual cleanings. Also, colored water in the bowl will tend to obscure medical symptoms such as the passing of blood during excretion or urination. Further, a persistent color in the toilet bowl water tends to obscure otherwise visible evidence of soiling on surfaces of the toilet bowl which are below the water line.

An object of the present invention is to provide a method of automatically sanitizing a toilet bowl with each flush.

Another object of the invention is to provide a visual color signal to indicate that the sanitizing agent is present and acting in the toilet bowl.

Another object of the invention is to provide a visual color signal which persists in the toilet bowl for only a short time after flushing.

Another object of the invention is to provide, by a visual color signal, a means by which the consumer will know when a new supply of sanitizing agent needs to be provided for the toilet.

DISCLOSURE OF INVENTION

The present invention relates to a method of treating a flush toilet, which comprises a flush tank and bowl, with a hypochlorite sanitizing agent each time the toilet is flushed, and providing a transitory visual signal to indicate the activity of the sanitizing agent in the bowl. The said method comprises the step of dispensing from separate dispensing means, into the flush water; (A) an aqueous solution of a compound which produces hypochlorite ion in aqueous solution; and (B) a solution of a dye, the said dye being one which is oxidized from a colored state to a colorless state in the bowl within about 5 seconds to 10 minutes (preferably about 10 seconds to about 5 minutes) after contact with the hypochlorite. If desired, the dye solution can also contain a water-soluble bromide salt to catalyze the activity of the hypochlorite.

The Sanitizing Agent

The sanitizing agent of the present invention can be any compound which provides the hypochlorite ion ($OCl^-$) in aqueous solution. Such compounds include alkali metal and alkaline earth metal hypochlorites, hypochlorite addition products, chloramines, chlorimines, chloramides, and chlorimides. Specific examples of compounds of this type include sodium hypochlorite, potassium hypochlorite, lithium hypochlorite, calcium hypochlorite, calcium hypochlorite dihydrate, monobasic calcium hypochlorite, dibasic magnesium hypochlorite, chlorinated trisodium phosphate dodecahydrate, potassium dichloroisocyanurate, sodium dichloroisocyanurate, sodium dichloroisocyanurate dihydrate, 1,3-dichloro-5,5-dimethylhydantoin, N-chlorosulfamide, Chloramine T, Dichloramine T, Chloramine B, Dichloramine B, and Di-Halo (bromochlorodimethyl hydantoin). A particularly preferred sanitizing agent composition suitable for use in the practice of the present invention is described in the commonly assigned U.S. patent application of John Daniel Nyquist entitled DISINFECTING COMPOSITION, Ser. No. 897,478, filed Apr. 18, 1978, said patent application being incorporated herein by reference. The composition described in the Nyquist application is a compacted cake comprising lithium hypochlorite and calcium hypochlorite in a ratio of lithium hypochlorite:calcium hypochlorite of from about 0.58:1 to about 0.17:1, by weight.

By virtue of the strong oxidizing power of the hypochlorite ion, it is highly effective in bleaching stains, breaking down and removing soils and killing microorganisms, thereby providing effective sanitizing action to the toilet bowl.

The amount of hypochlorite-providing compound dispensed to the toilet in the process of the invention can vary over a wide range, but preferably should be sufficient to provide from about 2 to about 30 ppm (preferably from about 4 to about 8 ppm) available chlorine in the bowl water at the end of the flush. Only a very small amount of the available chlorine which is delivered to the bowl will be utilized in oxidizing the dye. The sanitizing agent can be formulated as an aqueous liquid if it is to be dispensed from a dispensing means designed to receive liquids. The sanitizing agent can also be formulated into the form of a solid cake for use in dispensing means which are designed to receive a cake of solid material (see description of dispensing means below). The level of available chlorine in the bowl water can be measured by well-known methods such as the DPD Ferrous Titrametric Method or the Stabilized Neutral Orthotolidine Method, described, respectively, at pages 129 and 126 of Standard Methods for the Examination of Water and Wastewater, 13th Ed., published by American Public Health Association.

If desired, the activity of the hypochlorite can be catalyzed by addition of bromide ion to the process of the invention. This will enhance the sanitizing activity of hypochlorite in the toilet bowl, and will speed up the oxidation of the dye. Generally, any compound which produces bromide ion in aqueous solution can be used as the source of bromide ion. Examples of such compounds are inorganic bromide salts such as sodium bromide, potassium bromide, calcium bromide, zinc bromide, magnesium bromide and lithium bromide, as well as organic salts such as cetylpyridinium bromide and cetyltrimethylammonium bromide. The bromide salt is kept separate from the hypochlorite sanitizing agent until the sanitizing agent is dispensed into the flush water, i.e., the bromide and sanitizing agent are dispensed from separate dispensing means. Preferably, the bromide salt is dispensed to the toilet from the same dispensing means as the dye. When a bromide catalyst is used, the amount which is used preferably should be sufficient to provide a weight ratio of available chlorine to bromine ion of from about 2:1 to about 150:1, and most preferably from about 4:1 to about 13:1 in the toilet bowl. (All percentages and ratios herein are "by weight" unless specified otherwise.)

Dyes

A water-soluble bleachable dye is an essential feature of the present invention. The dye should be soluble in water to the extent of at least 0.01% by weight in water at 25° C.

The amount of dye dispensed to the toilet in the process of the invention will depend on the color intensity desired, the amount of sanitizing agent dispensed into the toilet with the dye, and on the quickness with which it is desired to have the color disappear. Generally, the amount of dye dispensed will be sufficient to produce a dye concentration of from about 0.02 to about 2 ppm, preferably from about 0.2 ppm to about 1.5 ppm in the toilet bowl. Generally, the dye should be present in a ratio of available chlorine:dye of from 2:1 to about 150:1, preferably from about 5:1 to about 25:1. Dye concentration and ratios herein are based upon the amount of the actual dye compound, unless specified otherwise. Dyes are normally sold in the form of mixtures of dye compound and inert diluent.

Dyes which are suitable for use in the method of the present invention are those which are oxidized by the sanitizing agent to a colorless state within a period of from about 5 seconds to 10 minutes from the time they come into contact with the sanitizing agent during the flushing of the toilet. A wide variety of oxidizable dyes can be utilized in the present process.

The following screening test can be used for determining the suitability of any particular dye for use in the method of the present invention. The test is conducted at pH 6 and pH 9, since this represents the range of pH's likely to be found in tap water.

Three liters of deionized water at 65° F. are placed in a four liter beaker, and the water is kept in stirring motion with a magnetic stirrer. 65° F. was chosen because it is approximately the median temperature for toilet flush water, which generally can vary in the range of 40° F. to 80° F. The appropriate amount of sodium hypochlorite is added via a pipette to the water from a 1% available chlorine aqueous stock solution of sodium hypochlorite. The pH is then adjusted to 6 or 9 with a one percent aqueous solution of NaOH or $H_2SO_4$, as needed. If bromide catalysis is utilized, the appropriate amount of sodium bromide is added from an aqueous stock solution (1% NaBr in water). The color change reaction is initiated by the addition of the appropriate amount of a stock solution of dye (0.1% dye, on an "as received" basis, in water). The solution is then observed to determine the time for disappearance of color.

The following table presents data on the testing of various dyes for suitability for use in the present invention with an available chlorine level of 5 ppm, catalyzed with 1.0 ppm bromide ion, and uncatalyzed. The dye level in all instances was 1 ppm on an "as received" basis. Based upon information provided by suppliers of the dyes, the approximate concentrations of actual dye were calculated and are shown in the table. The table records the time interval (M=minutes, S=seconds) from when the dye solution is added until the color disappears in the breaker.

TABLE I

| | | pH 6 | | pH 9 | |
|---|---|---|---|---|---|
| Dye* | Conc. ppm | 5 ppm Av. $Cl_2$ | 5 ppm Av. $Cl_2$ 1.0 ppm $Br^-$ | 5 ppm Av. $Cl_2$ | ppm Av. $Cl_2$ 1.0 ppm $Br^-$ |
| 1 | 0.92 | >10 M | >10 M | >10 M | >10 M |
| 2 | 0.90 | >10 M | >10 M | 6 M | 15 S |
| 3 | 0.88 | >10 M | >10 M | >10 M | >10 M |
| 4 | 0.68 | >10 M | >10 M | >10 M | >10 M |
| 5 | 0.95 | >10 M | 1 M | 8 M | 1.3 M |
| 6 | 0.25 | 1 M | 4 M | 6 M | 15 S |
| 7 | 0.90 | >10 M | 9 M | 2 M | 1.5 M |
| 8 | 1.0 | 4.5 M | 2.5 M | 1.8 M | 1.8 M |
| 9 | 0.13 | >10 M | 3.5 M | 7 M | 1 M |
| 10 | 0.29 | 1.5 M | 10 S | 8 M | 1.5 M |
| 11 | 0.85 | 6 M | 2 M | >10 M | 3 M |
| 12 | 0.75 | >10 M | 3.5 M | 6 M | 1.5 M |

*Dye identification (C.I. refers to the Color Index listing name or number)

| | |
|---|---|
| 1 FD&C Blue #1 | C.I. 42090 |
| 2 FD&C Blue #2 | C.I. 73015 |
| 3 FD&C Green #3 | C.I. 42053 |
| 4 Disulphine Blue VN | C.I. 42045 |
| 5 Alizarine Light Blue B | C.I. 63010 |
| 6 Carta Blue VP | C.I. 24401 |
| 7 Acid Green 2G | C.I. 42085 |
| 8 Astrazon Green D | C.I. 42040 |
| 9 Supranol Cyanine 7B | C.I. 42675 |
| 10 Maxilon Blue 3RL | C.I. Basic Blue 80 |
| 11 Drimarene Blue Z-RL | C.I. Reactive Blue 17 |
| 12 Alizarine Light Blue H-RL | C.I. Acid Blue 182 |

From these data it can be seen that for uncatalyzed hypochlorite at 5 ppm Av. $Cl_2$, dyes 6, 8, and 10 provide a color-to-colorless signal in the required time frame at both pH's. For bromide-catalyzed hypochlorite at 5 ppm Av.$Cl_2$ and 1 ppm bromide, dyes 5, 6, 7, 8, 9, 10, 11, and 12 provide a color-to-colorless signal in the required time frame at both pH's.

Optionally, the dyes used in the method of the present invention can be formulated into compositions containing other ingredients which it is desired to dispense into the toilet bowl, such as, for example, surfactants, sequestering agents, perfumes, and diluents such as water, organic solvents such as ethanol, and organic or inorganic salts such as sodium sulfate, sodium chloride and sodium acetate.

Surfactants can provide enhanced sanitizing performance through breakup and emulsification of soils, and also provide some sudsing in the toilet bowl, which may be aesthetically desirable. Perfumes provide a pleasant smell to the area surrounding the toilet and also help to obscure the "bleach" smell of the sanitizing agent. Sequestrants aid soil removal by sequestration of multivalent metal ions.

When the dyes herein are formulated with surfactants, the resulting compositions will generally comprise from about 5% to about 99% surfactant and from about 0.2% to about 15% dye. Perfumes will normally be used at levels of up to about 25% and inert diluents at levels up to about 90%. Sequestering agents such as potassium pyrophosphate, sodium tripolyphosphate and ethylenediamine pentaacetate can be used at levels up to about 25%.

Compositions comprising the dye and a surfactant and/or other ingredients can be conveniently pressed into the form of a cake for use in dispensers which are designed to receive a cake of solid material (see description of dispensing means, below). Such cakes can be made by extrusion or hydraulic stamping, or by pouring a melt of the composition into a mold and solidifying the composition by cooling.

If it is desired to use a dispensing means which is designed to receive liquids, the dye and any optional ingredients such as surfactants, etc., can be formulated into liquid compositions.

Dyes 8 and 10 in Table I are cationic dyes, whereas the remainder are anionic. When surfactants are to be used in the present invention, it is important that dye and surfactant be selected so as to be compatible with each other. Cationic dyes should not be used with anionic surfactants, and anionic dyes should not be used with cationic surfactants.

Anionic surfactants operable in compositions suitable for use in practicing the present invention can be broadly described as the water-soluble salts, particularly the alkali metal salts, of organic sulfuric acid reaction products having in their molecular structure an alkyl or alkaryl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic surfactants which can be employed in the practicing of the present invention are the sodium or potassium alkyl sulfates, especially those obtained by sulfating the higher alcohols ($C_8$–$C_{18}$ carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); paraffin sulfonate surfactants having the general formula $RSO_3M$, wherein R is a primary or secondary alkyl group containing from about 8 to about 22 carbon atoms (preferably 10 to 18 carbon atoms) and M is an alkali metal, e.g., sodium or potassium; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 10 moles of ethylene oxide; sodium or potassium salts of alkyl phenol ethylene oxide ether sulfates with about 1 to about 10 units of ethylene oxide per molecule and in which the alkyl radicals contain from about 8 to about 12 carbon atoms; the reaction products of fatty acids esterified with isethionic acid and neutralized with sodium hydroxide where, for example, the fatty acids are derived from coconut oil; sodium or potassium salts of fatty acid amides of a methyl tauride in which the fatty acids, for example, are derived from coconut oil and sodium or potassium $\beta$-acetoxy- or $\beta$-acetamido-alkanesulfonates where the alkane has from 8 to 22 carbon atoms.

Nonionic surfactants which can be used in practicing the present invention can be of three basic types—the alkylene oxide condensates, the amides and the semipolar nonionics.

The alkylene oxide condensates are broadly defined as compounds produced by the condensation of alkylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble-compound having the desired degree of balance between hydrophilic and hydrophobic elements.

Examples of such alkylene oxide condensates include:

1. The condensation products of aliphatic alcohols with ethylene oxide. The alkyl chain of the aliphatic alcohol can either be straight or branched and generally contains from about 8 to about 22 carbon atoms. Examples of such ethoxylated alcohols include the condensation product of about 6 moles of ethylene oxide with 1 mole of tridecanol, myristyl alcohol condensed with about 10 moles of ethylene oxide per mole of myristyl alcohol, the condensation product of ethylene oxide with coconut fatty alcohol wherein the coconut alcohol is a mixture of fatty alcohols with alkyl chains varying from 10 to 14 carbon atoms and wherein the condensate contains about 6 moles of ethylene oxide per mole of alcohol, and the condensation product of about 9 moles of ethylene oxide with the abovedescribed coconut alcohol. Examples of commercially available nonionic surfactants of this type include Tergitol 15-S-9 marketed by the Union Carbide Corporation, Neodol 23-6.5 marketed by the Shell Chemical Company and Kyro EOB marketed by The Procter & Gamble Company.

2. The polyethylene oxide condensates of alkyl phenols. These compounds include the condensation products of alkyl phenols having an alkyl group containing from about 6 to about 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds can be derived, for example, from polymerized propylene, diisobutylene, octene, or nonene. Examples of compounds of this type include nonyl phenol condensed with about 9.5 moles of ethylene oxide per mole of nonyl phenol, dodecyl phenol condensed with about 12 moles of ethylene oxide per mole of phenol, dinonyl phenol condensed with about 15 moles of ethylene oxide per mole of phenol, di-isooctylphenol condensed with about 15 moles of ethylene oxide per mole of phenol. Commercially available nonionic surfactants of this type include Igepal CO-610 marketed by the GAF Corporation; and Triton X-45, X-114, X-100 and X-102, all marketed by the Rohm and Haas Company.

3. The condensation products of ethylene oxide with a hydrophobic base formed by the condensation of propylene oxide with propylene glycol. The hydrophobic portion of these compounds has a molecular weight of from about 1500 to 1800 and of course exhibits water insolubility. The addition of polyoxyethylene moieties of this hydrophobic portion tends to increase the water-solubility of the molecule. Examples of compounds of this type include certain of the commercially available Pluronic surfactants marketed by the Wyandotte Chemicals Corporation.

4. The condensation products of ethylene oxide with the product resulting from the reaction of propylene oxide and ethylene diamine. The hydrophobic base of these products consists of the reaction product of ethylene diamine and excess propylene oxide, said base having a molecular weight of from about 2500 to about 3000. This base is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds marketed by the Wyandotte Chemicals Corporation.

Examples of the amide type of nonionic surfactants include the ammonia, monoethanol and diethanol amides of fatty acids having an acyl moiety of from about 8 to about 18 carbon atoms. These acyl moieties are normally derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process.

Examples of the semi-polar type of nonionic surfactants are the amine oxides, phosphine oxides and sulfoxides. These materials are described more fully in U.S. Pat. No. 3,819,528, Berry, issued June 25, 1974, and incorporated herein by reference.

Ampholytic surfactants which can be used in practicing the present invention can be broadly described as derivatives of aliphatic amines which contain a long chain of about 8 to about 18 carbon atoms and an anionic water-solubilizing group, e.g., carboxy, sulfo and sulfato. Examples of compounds falling within this definition are sodium-3-dodecylamino-propionate, sodium-3-dodecylamino propane sulfonate, and dodecyl dimethylammonium hexanoate.

Zwitterionic surfactants which can be used in practicing the present invention are broadly described as internally-neutralized derivatives of aliphatic quaternary ammonium and phosphonium and tertiary sufonium compounds, in which the aliphatic radical can be straight chain or branched, and wherein one of the aliphatic substituents contains from about 8 to about 18 carbon atoms and one contains an anionic water-solubilizing group, e.g., carboxy, sulfo, sulfato, phosphato, or phosphono.

Cationic surfactants which can be used in practicing the present invention include stearyl dimethyl benzyl ammonium chloride, coconut dimethyl benzyl ammonium chloride, cetyl pyridinium chloride and cetyl trimethyl ammonium chloride.

Bleach-stable (i.e., hypochlorite-stable) surfactants which are especially resistant to oxidation are the alkyl sulfates and paraffin sulfonates. Alkyl sulfates are the water-soluble salts of sulfated fatty alcohols containing from about 8 to about 18 carbon atoms in the alkyl group. Examples of suitable alcohols which can be employed in alkyl sulfate manufacture include decyl, lauryl, myristyl, palmityl and stearyl alcohols and the mixtures of fatty alcohols derived by reducing the glycerides of tallow and coconut oil.

Specific examples of alkyl sulfate salts which can be employed in the instant surfactant/dye compositions include sodium lauryl alkyl sulfate, sodium stearyl alkyl sulfate, sodium palmityl alkyl sulfate, sodium decyl sulfate, sodium myristyl alkyl sulfate, potassium lauryl alkyl sulfate, potassium stearyl alkyl sulfate, potassium decyl sulfate, potassium palmityl alkyl sulfate, potassium myristyl alkyl sulfate, sodium dodecyl sulfate, potassium dodecyl sulfate, potassium tallow alkyl sulfate, sodium tallow alkyl sulfate, sodium coconut alkyl sulfate, potassium coconut alkyl sulfate and mixtures of these surfactants. Highly preferred alkyl sulfates are sodium coconut alkyl sulfate, potassium coconut alkyl sulfate, potassium lauryl alkyl sulfate and sodium lauryl alkyl sulfate.

Paraffin sulfonate surfactants have the general formula $RSO_3M$, wherein R is a primary or secondary alkyl group containing from about 8 to about 22 carbon atoms (preferably 10 to 18 carbon atoms) and M is an alkali metal, e.g., sodium or potassium. Paraffin sulfonate surfactants and methods for their preparation are well known in the art. They may be prepared, for example, by reaction of hydrocarbons with sulfur dioxide, oxygen and a sulfonation reaction initiator. Alternatively, they may be prepared by reacting an alkene and a sodium bisulfite under suitable radiation or catalysis, as disclosed in British Patent 1,451,228 published September 29, 1976, and hereby incorporated herein by reference. Paraffin sulfonate surfactants are commercially available, e.g., from Farbwerke Hoechst A.G.

Preferred paraffin sulfonates herein are secondary paraffin sulfonates. Examples of specific paraffin sulfonates herein are:

Sodium-1-decane sulfonate;
Potassium-2-decane sulfonate;
Lithium-1-dodecane sulfonate;
Sodium-6-tridecane sulfonate;
Sodium-2-tetradecane sulfonate;
Sodium-1-hexadecane sulfonate;
Sodium-4-octadecane sulfonate;
Sodium-3-octadecane sulfonate.

Normally, the paraffin sulfonates are available as mixtures of individual chain lengths and position isomers, and such mixtures are suitable for use herein.

Dispensing Means

In order to provide automatic sanitizing of the toilet bowl in accordance with the present invention, it is essential that the hypochlorite sanitizing agent and the dye, in the form of relatively concentrated solutions, be dispensed into the flush water each time the toilet is flushed.

It is within the contemplation of the present invention that the concentrated solution of one of the components (i.e., either the dye or the sanitizing agent) be dispensed into the flush tank during the refill after a flush (thereby forming a dilute solution of one component in the flush water which is stored in the tank between flushes) and that the concentrated solution of the other component be dispensed into this treated flush water during the time it is flowing from the tank to the bowl during the next succeeding flush. Dispensing means which operate to dispense solutions into a toilet tank during the time it is refilling are described, for example, in U.S. Pat. Nos. 1,798,090, Lebegue, issued Mar. 24, 1931; 3,339,801, Hronas, issued Sept. 5, 1967; and 3,121,236, Yodro et al., issued Feb. 18, 1964.

It is preferred that both of the concentrated solutions be dispensed into the flush water on the downflush, i.e., that they be dispensed into the flush water during the time the flush water is flowing from the tank into the bowl. In this preferred mode of operation, it is additionally preferred that the dispensing of the hypochlorite and dye should occur near the end of the flush in order to avoid wastage of dye and hypochlorite and to keep to a minimum the time of contact between dye and hypochlorite before they enter the bowl. The respective dispensing means for the hypochlorite and dye solutions should preferably be positioned relative to each other in the toilet tank so that these concentrated solutions will be diluted by flush water during the flush before they come into contact with each other, i.e., intimate mixture of streams of the two concentrated solutions in the flush tank should preferably be avoided. Dispensing means for automatically dispensing solutions of chemicals into the flush water during the down-flush are well known to the art. U.S. Pat. No. 3,504,384, Radley et al., issued Apr. 7, 1970, discloses a dual dispenser for separately dispensing a detergent/dye solution and a hypochlorite solution into the flush water during the flush. Water from the flush tank flows into the respective dispenser chambers as the tank fills after a flush, where it comes into contact with a solid detergent/dye composition and a solid hypochlorite-producing composition in the respective chambers. During the interval between flushes, relatively concentrated solutions of the hypochlorite and detergent/dye compositions form in the respective chambers, and these solutions are discharged into the flush water on the next flush. It should be noted that the inlet and outlet ports of the dispenser chambers in the Radley et al. dual dispenser are not closed between flushings, and therefore there is opportunity for ingredients in the respective concentrated solutions in the chambers to diffuse into the tank water between flushes, whereby there is also opportunity for ingredients from one dispenser chamber to ultimately find their way into the solution in the other dispenser chamber. The longer the time interval between flushes, the more likelihood there is that some portion of the contents of the two dispenser chambers will have an opportunity to come into contact with each other before they are dispensed into the flush water on the next flush. While dispensing devices of the type disclosed in Radley et al. can be used in the method of the present invention, they are not preferred. Because of the high reactivity between the dye and the hypochlorite, the color intensity and duration of the color signal in the bowl will be less reproducible from one flush to the next than if the dye and sanitizing agent are substantially completely isolated from the tank water (and, therefore, from each other) between flushes. This isolation can be accomplished in the dispensing means by providing a blocking means such as an air bubble or a mechanical seal which, during the period between flushes, blocks the ports by which liquid flows into and out of the dispensing means. Depending on the type dispensing means used, and the materials used in constructing it, complete isolation of the concentrated solutions from the tank water may not always be possible since some small amount of solution may escape by capillary action, imperfect sealing of the inlet and outlet ports, etc.

Dispensers which completely or substantially completely isolate their contents from the tank water during the quiescent period between flushes are known to the art and are the preferred type for use in the present invention. Such dispensers are disclosed, for example, in U.S. Pat. No. 3,831,205, issued Aug. 27, 1974, to Foley; U.S. Pat. No. 3,341,074, issued Sept. 12, 1967, to Panutti; U.S. Pat. No. 4,036,407, issued July 19, 1977, to Slone; U.S. Pat. No. 4,171,546, issued Oct. 23, 1979, to Dirksing; and U.S. Ser. No. 879,469, Dirksing, entitled PASSIVE DOSING DISPENSER EMPLOYING TRAPPED AIR BUBBLE TO PROVIDE AIRLOCK, filed Apr. 18, 1978, and abandoned in favor of U.S. Ser. No. 002,524, Dirksing, filed Jan. 11, 1979. All of the foregoing patents and applications are incorporated herein by reference.

Preferably, the amount of sanitizing composition placed in the sanitizing composition dispensing means should be chosen so as to last at least as long as (i.e., through at least as many flushes as) the amount of dye composition in the dye composition dispensing means. When the consumer no longer sees any color appear in the bowl when flushing the toilet, this indicates that it is time to replace the system (dye and sanitizer). Conversely, if the consumer sees that color persists in the toilet bowl, this is also an indication that the supply of sanitizing agent has been exhausted and the system should be replaced. As indicated previously, it is undesirable to have a persistent color in the toilet bowl between flushes, and, therefore, it is preferable that the supply of sanitizer last for at least as long as the supply of dye.

The dye and sanitizing agents can be formulated into the form of liquid or solid composition for use in present method. The form of the composition will depend upon the type of dispenser used. The most preferred dispensers are those which are designed to receive a solid composition. With this type of dispenser, water from the flush tank enters into the dispenser during the refill of the flush tank at the end of the flush. Water within the dispenser remains in contact with the solid composition between flushes, thereby forming a concentrated solution within the dispenser. When the toilet is flushed, a predetermined amount of the concentrated solution is discharged into the flush water as it flows from the tank to the bowl. Particularly preferred dispensers which are designed to receive a solid composition are those of the type disclosed in Dirksing U.S. Pat. No. 4,171,546 and application Ser. No. 897,469 supra. In a preferred embodiment, these two types of dispensing means are constructed into a dual dispenser unit, as is set forth in Example I, herein.

EXAMPLE I

A solid, compacted sanitizing composition cake was prepared by dry-mixing FORM-2 lithium hypochlorite (30% LiOCl), as available from Lithium Corporation of America, Bessemer City, N.C., with HTH calcium hypochlorite [65% $Ca(OCl)_2$], as available from Olin Mathieson Chemical Corp., NaCl and $Na_2SO_4$ in the proportions hereinafter set forth and subjecting the granular mixture to a compaction pressure of about 2.5 tons per square inch on a Stokes Model R Tablet Press:

| Ingredient | Grams |
|---|---|
| LiOCl (Form 2) | 27.2 |
| HTH [65% $Ca(OCl)_2$] | 43.9 |
| NaCl | 21.7 |
| $Na_2SO_4$ | 7.2 |

| Ingredient | Grams |
| --- | --- |
| | 100.0 |

This composition had a LiOCl:Ca(OCl)$_2$ weight ratio of about 0.29:1, and an available chlorine level (AvCl$_2$) of about 38% to 39%. The cake had a specific gravity of about 1.7, and dimensions of about 3.5 inches by about 1.5 inches by about 0.625 inches.

A solid, compacted cake containing dye was prepared by mixing the ingredients hereinafter set forth in a batch amalgamator, followed by milling and then extrusion to form a rectangular slab having dimensions of about 3.625 inches in width by about 2.0 inches in height by about 0.5 inches thick, and a specific gravity of about 1.1.

| Ingredient | Grams |
| --- | --- |
| Sodium paraffin sulfonate (Hostapur, approximately 84% active, as available from American Hoechst, Somerville, N.J.) | 52.2 |
| Acid Green 2G Conc. (as available from Sandoz, Hanover, N.J.) | 3.7* |
| NaBr | 1.9 |
| Perfume | 7.2 |
| | 65.0 |

*The dye sample contained 10% diluent, therefore, the actual dye level was 3.3 grams.

This dye cake was thereafter coated with talcum powder to prevent it from sticking to the sides of the dispensing apparatus.

The solid sanitizer cake and dye cake were incorporated, respectively, into separately dispensing compartments of a dual dispensing apparatus which was vacuum thermoformed in two segments from 0.015 inch thick polyvinyl chloride. The configuration of the integrally formed dual compartment dispenser was such that the dye cake was placed vertically overhead the sanitizer cake. The portion of the dispensing apparatus housing the dye cake was of a configuration generally similar to those described in connection with FIGS. 1 and 15 of the aforementioned patent application of Robert S. Dirksing, Ser. No. 897,469, filed Apr. 18, 1978, while the portion of the dispensing apparatus housing the sanitizer cake was of a configuration generally similar to that described in connection with FIG. 12 of the aforementioned patent of Robert S. Dirksing, U.S. Pat. No. 4,171,546, issued Oct. 23, 1979. These separate portions of the dispensing apparatus (actually two separate dispensing means) produce concentrated solutions, respectively, of the sanitizer composition and dye composition in water which enters the apparatus when the toilet tank is filling after a flush. The respective dispensing means serve to isolate the concentrated solutions from each other and from the tank water during the period between flushes, although a very small amount of dye solution was found to migrate into the flush tank between flushes. The positioning of the respective dispensing means of the dual dispenser is such as to prevent mixing of the dispensed sanitizer and dye solutions during the flush until they have been diluted with flush water. The measuring cavity and inlet conduit of the sanitizer-containing portion of the dual dispenser is so sized that approximately 9 cubic centimeters of sanitizer-containing solution is dispensed with each flush cycle of the toilet. The dye-containing portion of the dispenser is so sized that approximately two cubic centimeters of dye-containing solution is dispensed into the flush water as it leaves the tank during each flush cycle of the toilet.

The aforedescribed exemplary embodiment of a dual dispenser for carrying out the cleansing and disinfecting method of the present invention provides an excellent release of both the sanitizer-containing solution and the surfactant-containing solution throughout the life of the unit.

A conventional toilet comprising a flush tank and a bowl was equipped with this type dual dispenser by placing the dispenser into the tank. Over a 20-day period the toilet was flushed daily at predetermined time intervals during each day. Observations of color in the bowl during and after flushing were made periodically. The toilet was flushed a total of 281 times. The first seven flushes are required to prime the dispensing means for the hypochlorite sanitizer. Accordingly, on the first seven flushes very little, if any, hypochlorite was delivered to the bowl, and the color which was delivered to the bowl persisted between flushes. After the seventh flush, color observations were made on 47 of the remaining flushes. Out of this total of 47 observations, there was one instance in which no color was seen in the bowl, either during or after the flush was complete. In all other instances color was observed during the flush and at the end of the flush. The time of color persistence ranged from 10 seconds to 120 seconds from the end of flush (i.e., from the time when the siphon breaks and the bowl begins to refill). The flush itself takes about 13 seconds (from beginning of tank water flow until siphon break), therefore, the total time for color persistence was from about 23 seconds to about 133 seconds. The amount of available chlorine in the bowl at the end of the flush averaged about 6 ppm.

What is claimed is:

1. A method of sanitizing a toilet which comprises a flush tank and a bowl, with a hypochlorite sanitizing agent each time the toilet is flushed, and providing a transitory visual signal to indicate the activity of the sanitizing agent in the bowl, said method comprising the step of dispensing, from separate dispensing means, into the flush water,
    (A) an aqueous solution of a compound which produces hypochlorite ion in aqueous solution, and
    (B) a solution of a dye selected from the group consisting of those identified by Color Index numbers 24401 and 42040, and Color Index name Basic Blue 80;

the amount of (A) being sufficient to produce a concentration of from about 2 to about 30 ppm available chlorine in the bowl water at the end of the flush, the amount of (B) being sufficient to produce a dye concentration of from about 0.02 to about 2 ppm and an available chlorine:dye ratio of from about 2:1 to about 150:1, and the pH of the solution formed in the toilet bowl being from about 6 to about 9.

2. The method of claim 1 wherein the respective solutions, (A) and (B), are both dispensed into the flush water during the down-flush.

3. The method of claim 2, wherein the respective solutions, (A) and (B), are substantially completely isolated from the flush water in the toilet tank during the quiescent period between flushes of the toilet.

4. The method of claim 3 wherein the amount of sanitizing agent dispensed is sufficient to produce a concentration of from about 4 to about 8 ppm available chlorine in the bowl water at the end of the flush.

5. The method of claim 4 wherein the available chlorine to dye ratio is from about 5:1 to about 25:1.

6. A method of sanitizing a toilet bowl which comprises a flush tank and a bowl, with a bromide-catalyzed hypochlorite sanitizing agent each time the toilet is flushed, and providing a transitory visual signal to indicate the activity of the sanitizing agent in the bowl, said method comprising the step of dispensing, from separate dispensing means, into the flush water, (A) an aqueous solution of a compound which produces hypochlorite ion in aqueous solution, and (B) a solution comprising a dye and a water-soluble bromide salt, the said bromide salt being present in sufficient quantity to catalyze the oxidizing action of the hypochlorite-producing compound of (A) in the bowl, the said dye being selected from the group of those identified by Color Index numbers 24401, 42040, 63010, 42085, 42675, and those having Color Index names Basic Blue 80, Reactive Blue 17 and Acid Blue 182;

the amount of (A) being sufficient to produce a concentration of from about 2 to about 30 ppm available chlorine in the bowl, the amount of (B) being sufficient to produce a dye concentration of from about 0.2 to about 2 ppm and an available chlorine:dye ratio of from about 2:1 to 150:1 in the bowl, and the pH of the solution formed in the bowl being from about 6 to about 9.

7. The method of claim 6 wherein the dye is Color Index number 42085.

8. The method of claim 6 wherein the respective solutions, (A) and (B), are both dispensed into the flush water during the down-flush.

9. The method of claim 8 wherein the respective solutions, (A) and (B), are substantially completely isolated from the flush water in the toilet tank water during the quiescent period between flushes of the toilet.

10. The method of claim 9 wherein the amount of bromide salt in (B) is sufficient to produce a weight ratio of available chlorine to bromide ion of from about 2:1 to about 150:1 in the toilet bowl water at the end of the flush.

11. The method of claim 9 wherein the amount of hypochlorite-producing compound dispensed is sufficient to produce a concentration of from about 4 to about 8 ppm available chlorine in the toilet bowl at the end of the flush, and the amount of bromide salt dispensed is sufficient to produce a weight ratio of available chlorine to bromide of from about 4:1 to about 13:1.

12. The method of claim 11 wherein the available chlorine to dye ratio is from about 5:1 to about 25:1.

13. The method of claim 12 wherein the dye is Color Index number 42085.

* * * * *